United States Patent [19]
Adams

[11] Patent Number: 6,135,950
[45] Date of Patent: Oct. 24, 2000

[54] E-FIT MONITOR

[76] Inventor: Tadd O. Adams, P.O. Box 345, Eastontown, N.J. 07724

[21] Appl. No.: 09/314,931

[22] Filed: May 20, 1999

Related U.S. Application Data

[60] Provisional application No. 60/098,139, Aug. 27, 1998.

[51] Int. Cl.<sup>7</sup> ..................................................... A61B 5/00
[52] U.S. Cl. ........................................ 600/300; 600/586
[58] Field of Search ........................... 434/127; 600/586; 128/904, 903

[56] References Cited

U.S. PATENT DOCUMENTS

| | | | |
|---|---|---|---|
| 4,672,976 | 6/1987 | Knroll | 600/586 |
| 4,796,182 | 1/1989 | Duboff | |
| 4,823,808 | 4/1989 | Clegg et al. | 128/903 |
| 4,951,197 | 8/1990 | Mellinger | |
| 5,263,491 | 11/1993 | Thornton | 600/587 |
| 5,301,679 | 4/1994 | Taylor | 600/586 |
| 5,388,043 | 2/1995 | Hettinger | |
| 5,412,564 | 5/1995 | Ecer | |
| 5,722,418 | 3/1998 | Bro et al. | 600/300 |

*Primary Examiner*—Robert L. Nasser
*Assistant Examiner*—Michael Astorino
*Attorney, Agent, or Firm*—Patent & Trademark Services; Joseph H. McGlynn

[57] ABSTRACT

A diet aid which has a pager size device worn by a user to aid them in controlling their daily food intake. The device monitors their daily food intake and sounds an alarm when the volume of food reaches a set point limit. In addition the device utilizes a sensor placed near the user's Adams apple to monitor the swallowing rate and another sensor placed near the user's heart to monitor their heart rate.

7 Claims, 1 Drawing Sheet

E-FIT MONITOR

This is a conversion to a Utility application of Provisional application 60/098,139, filed Aug. 27, 1998.

BACKGROUND OF THE INVENTION

This invention relates, in general, to diet aids, and, in particular, to a pager size device which is used to aid in controlling a person's daily food intake.

DESCRIPTION OF THE PRIOR ART

In the prior art various types of diet aids have been proposed. For example, U.S. Pat. No. 4,796,182 to Duboff discloses an electronic device for displaying preset amounts of food categories allowable in a person's daily diet.

U.S. Pat. No. 4,951,197 to Mellinger discloses a weight loss management system which uses a computer to analyze a person's past medical history eating habits, etc. and to provide a menu to allow that person to maintain a specific weight.

U.S. Pat. No. 5,388,043 to Hettinger discloses a device which assesses the intake of food and a printer to print out suggested changes in a person's eating habits.

U.S. Pat. No. 5,412,564 to Ecer discloses a computer system for storing and processing nutritional information used for diet control.

SUMMARY OF THE INVENTION

The present invention is directed to a diet aid which has a pager size device worn by a user to aid them in controlling their daily food intake. The device monitors their daily food intake and sounds an alarm when the volume of food reaches a set point limit. In addition the device utilizes a sensor placed near the user's Adams apple to monitor the swallowing rate and another sensor placed near the user's heart to monitor their heart rate.

It is an object of the present invention to provide a new and improved diet aid.

It is an object of the present invention to provide a new and improved diet aid which monitors a person's daily food intake and sound an alarm when a set point limit has been reached.

It is an object of the present invention to provide a new and improved diet aid which monitors a person's daily food intake and their activity level.

These and other objects and advantages of the present invention will be fully apparent from the following description, when taken in connection with the annexed drawings.

DESCRIPTION OF THE PREFERRED EMBODIMENT

Figure 1:
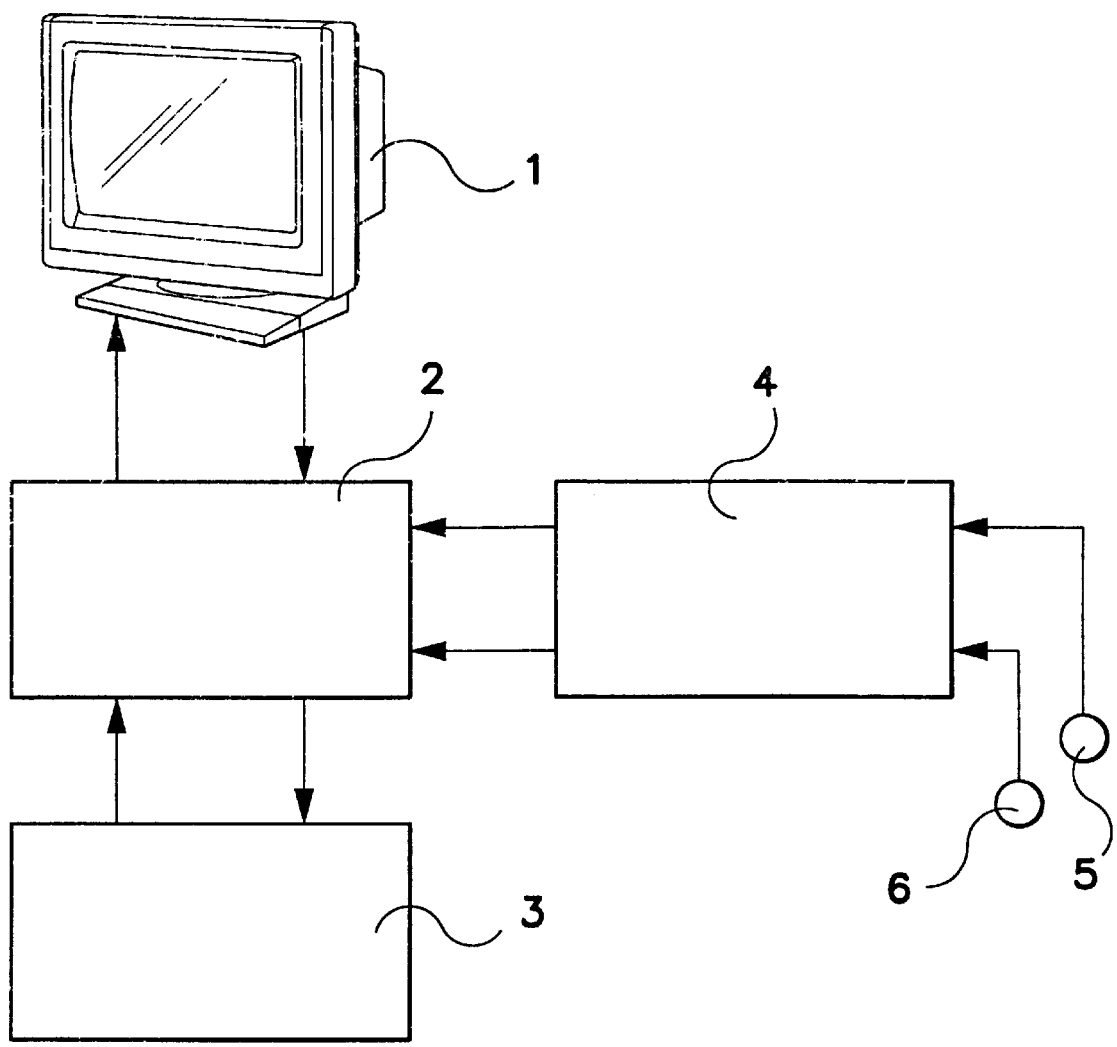
FIG. 1 is schematic view of the components used with the present invention.
Figure 2:
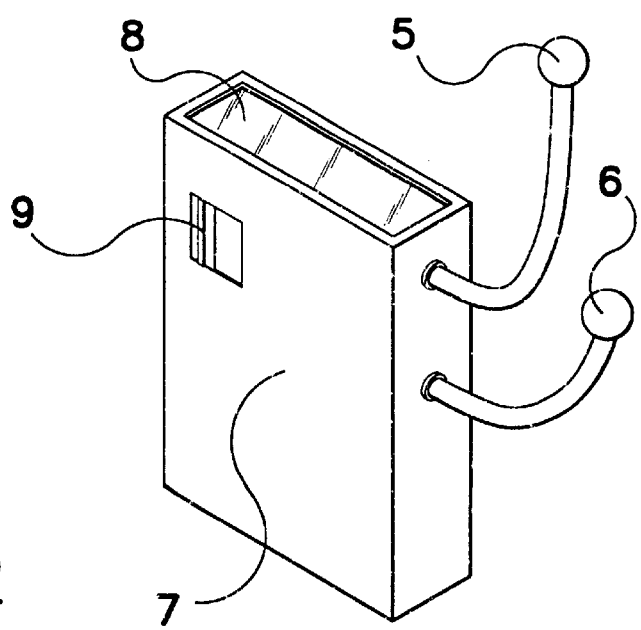
FIG. 2 is a view of the pager size device of the present invention which is worn by the user.

Referring now to the drawings in greater detail, FIG. 1 shows a schematic view of the components used with the present system. The system is controlled by information imparted from a conventional computer work station 1, as will be explained in greater detail below. The workstation 1 can be connected, by any conventional means, to the Central Processing Unit (CPU) 2 which is housed in the device 7 shown in FIG. 2. The CPU is connected to a non-volatile memory chip 3 which has stored therein digitized reference sounds for a purpose to be described below. In addition, the device 7 has a two channel sound chip 4, one channel will transfer information from the throat sensor 5 to the CPU, and a second channel which will transfer information from the chest sensor 6 to the CPU, as will be explained below.

In order to use the device of the present invention, a person would wear the unit 7 for a period of time in order for the CPU to collect reference data concerning their eating habits and their activity levels. The device can be attached to a person in any conventional way. One of the sensors 5, which can be any conventional sensor such as, but not limited to, a microphone will be attached to a person's throat in the vicinity of their Adams apple by any conventional means such as, but not limited to, adhesive. The other sensor 6, which can be any conventional sensor such as, but not limited to, a microphone will be attached to a person's chest in the vicinity of their heart by any conventional means such as, but not limited to, adhesive.

As the user goes about their normal daily routine, the sensor 5 will send data concerning the user's normal swallowing rate and their normal breathing rate to the CPU 2 along one channel of the sound chip 4. The sensor 6 will send data concerning the user's normal heart rate to the CPU 2 along another channel of the sound chip 4. The CPU will record the data and calculate limit set points as well as reference sounds of the person's swallowing and heart beat. The sound chip 4 will take the input from each of the sensors 5, 6 on separate channels to keep them separate, adjust the gain as necessary and output the separate digitized audio signals to the CPU 2. This will give the CPU a record of the normal swallowing and heart sounds of the user which will be stored in the memory chip 3.

Once the CPU has a record of the normal sounds it can then calculate limit set points which will enable the user to lose weight. The CPU can be connected to a workstation 1 which can be used to calibrate the CPU 2, and download results to a printer if necessary. At this point the device 7 can be used in the diet mode.

In the diet mode, the user again wears the device on his/her person and the sensors 5, 6 are attached to the same body parts as in the calibration mode. The sound chip 4 again takes the input from each of the two sensors 5, 6 on separate channels, and adjusts the gain and sends them to the CPU 2. The CPU will sample each of the channels and compare them to the reference sounds that were previously stored in the memory chip 3. One of the channels will compare breathing, swallowing or talking sound reference sounds with those previously stored and the other channel will compare heart rate sounds with those previously stored.

Each time the user swallows, for example, the CPU 2 will compare the sound with the sampled sound stored in memory chip 3. If the sound is the sound of the person swallowing, rather than the sound of the person talking for example, a swallow counter is incremented. From the swallow counter the CPU calculates a swallow rate. Based on the calibration data stored in the memory chip 3 the volume of food in the person's stomach is calculated based on the number of times the person swallows. If the swallow rate is too high (i.e. the person is eating too much or too fast) the device 7 will set off an alarm 9 (either an auditory or visual alarm or both) to alert the person to this fact, and a message will appear in the display 8. The messages could take different forms depending on what data the computer is receiving. If the person is eating too fast the message might state, "SLOW DOWN". If the calculated volume of the person's stomach reaches a set limit, as calculated by the CPU, the system will alarm the person and display a message, "STOMACH FULL".

The system will also track the per-day volume intake of the user. If the person exceeds a per-day maximum, an alarm will sound and display a message indicating this.

The second sensor 6 monitors the heart rate. The heart rate along with the respiratory rate are used to calculate the activity level of the person. If the person's activity level is increased, the per-day limit of the food intake is increased. If the activity level goes down, the limit is decreased.

In this way a user's food intake and activity level is constantly being monitored by the CPU. If the food intake (for either an individual meal or the full day) is exceeded, an alarm 9 will sound and a pertinent message will appear in the display 8 to indicate this and the person will be able to take steps to correct the imbalance, such as by eating less or increasing their physical activity. This will allow the person to control their caloric intake and thereby lose weight.

It should be noted that the alarm 9 and the visual display 8 are conventional devices well known in the art and, therefore, specific details of these devices are not necessary.

Although the E-Fit Monitor and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What I claim as my invention is:

1. A diet monitor comprising:
   a central processing unit,
   a memory chip means connected to said central processing unit for storing sound, and
   a sound chip means connected to said central processing unit for receiving sounds from at least two external sources and sending said sounds to said central processing unit, and
   means connected to said sound chip means for collecting sounds and sending said sounds to said sound chip means wherein said diet monitor has an alarm means for indicating to a person wearing said diet monitor that said person is eating too much.

2. The diet monitor as claimed in claim 1, wherein said means connected to said sound chip means for collecting sounds is a pair of microphones.

3. The diet monitor as claimed in claim 2, wherein said pair of microphones are connected to separate channels within said sound chip means,
   one of said microphones has means for connecting it to a persons throat, and another of said microphones has means for connecting it to a persons chest.

4. The diet monitor as claimed in claim 1, wherein said diet monitor has an alarm means for indicating to a person wearing said diet monitor that said person's activity rate is below a selected level.

5. The diet monitor as claimed in claim 1, wherein said diet monitor has a visual display means for sending a message to a person wearing said diet monitor relating to said person's eating.

6. The diet monitor as claimed in claim 4, wherein said diet monitor has a visual display means for sending a message to a person wearing said diet monitor relating to said person's activities.

7. A method of using a diet monitor,
   said diet monitor comprising:
      a central processing unit,
      a memory chip means connected to said central processing unit for storing sounds, and
      a sound chip means connected to said central processing unit for receiving sounds from at least two external sources and sending said sounds to said central processing unit, and
      means connected to said sound chip means for collecting sounds and sending said sounds to said sound chip means, and
         wherein said means connected to said sound chip means for collecting sounds is a pair of microphones, and
         wherein said diet monitor includes alarm means and a visual display means,
   said method comprises:
      attaching said diet monitor to a person,
      attaching one of said microphones to said person's throat,
      attaching another of said microphones to said person's chest,
      sending said person's throat sounds through one of said microphones to said sound chip means which sends said throat sounds to said central processing unit,
      sending said person's chest sounds through another of said microphones to said sound chip means which sends said chest sounds to said central processing unit,
      recording said throat sounds and said chest sounds in said memory chip means,
      using said central processing unit to calculate limit set points based on the throat sounds and the chest sounds,
      monitoring said persons throat sounds through said microphone attached to said person's throat,
      comparing said person's throat sounds with the calculated limit set points, and
      sounding a warning by means of said alarm means if the person's throat sounds exceed the calculated limit set points, and
      flashing a visual message by means of said visual display means, and
      monitoring said persons chest sounds through said microphone attached to said person's chest,
      comparing said person's chest sounds with the calculated limit set points, and
      sounding a warning by means of said alarm means if the person's chest sounds exceed the calculated limit set points, and
      flashing a visual message by means of said visual display means.

* * * * *